United States Patent [19]

Azria et al.

[11] Patent Number: 5,122,520
[45] Date of Patent: Jun. 16, 1992

[54] ACID ADDITION SALTS OF AMIDATED TAURINE OR GLYCINE, THEIR PREPARATION AND USE

[75] Inventors: Moise Azria, Basel; Zdenek Brich, Ormalinge, both of Switzerland

[73] Assignee: Sandoz Ltd., Basel, Switzerland

[21] Appl. No.: 659,788

[22] Filed: Feb. 22, 1991

Related U.S. Application Data

[63] Continuation of Ser. No. 509,005, Apr. 12, 1990, abandoned, which is a continuation of Ser. No. 345,595, May 1, 1989, abandoned.

[30] Foreign Application Priority Data

Apr. 30, 1988 [DE] Fed. Rep. of Germany ....... 3814694

[51] Int. Cl.$^5$ ............................ A61K 1/56; C07J 41/00
[52] U.S. Cl. ..................................... 514/171; 514/182; 552/554
[58] Field of Search ................. 552/554; 514/182, 171

[56] References Cited

U.S. PATENT DOCUMENTS

| | | | |
|---|---|---|---|
| 3,580,936 | 5/1971 | Patchett et al. | 260/397 |
| 3,839,565 | 10/1974 | Saltzman | 424/238 |
| 3,856,953 | 12/1974 | Saltzman | 424/238 |
| 4,104,285 | 8/1978 | Gallo-Torres et al. | 260/397.1 |
| 4,746,508 | 5/1988 | Carey et al. | 424/88 |

*Primary Examiner*—Werren B. Lone
*Assistant Examiner*—Kimberly J. Kestler
*Attorney, Agent, or Firm*—Gerald D. Sharkin; Robert S. Honor; Joseph J. Borovian

[57] ABSTRACT

Acid addition salt of taurine or glycine, their amino group being amidated with a carboxylic acid residue which contains the structure of a 3α, 7α, 12α-trihydroxysteroid, their acid group being neutralized with the amino group of an aliphatic amine or neutralized with the amino group of a basic α-amino carboxylic acid which group is connected over an alkylene bridge with the α-amino acid group, may be used e.g. as transmucuous resorption promoter of drug compounds.

15 Claims, No Drawings

ACID ADDITION SALTS OF AMIDATED TAURINE OR GLYCINE, THEIR PREPARATION AND USE

This is a continuation of application Ser. No. 07/509,005, filed Apr. 12, 1990 which in turn is a continuation of application Ser. No. 07/345,595, filed May 1, 1989, both now abandoned.

This invention relates to acid addition salts of amidated taurine or glycine, their preparation and use.

The invention provides, in one aspect, an acid addition salt of an anion of taurine or glycine wherein the amino group thereof is substituted by an acyl group of a 3α, 7α, 12α-trihydroxy steroid carboxylic acid, and a cation of either (a) an aliphatic amine, any substituents of which are other than carboxylic groups, or (b) a basic alpha amino acid having an alkylene bridge between the alpha amino acid group and another amino group.

Hereinafter these are referred to as acid addition salts of the invention.

The invention provides in another aspect a process for the production of an acid addition salt of the invention which comprises combining taurine or glycine wherein the amino group thereof is substituted by an acyl group of a 3α, 7α, 12α-trihydroxy steroid carboxylic acid with either (a) an aliphatic amine, any substituents of which are other than carboxyl groups or (b) a basic alpha amino acid having an alkylene bridge between the alpha amino acid group and another amino group.

The aliphatic amine may be, e.g. of 1 to 10 carbon atoms.

The aliphatic amine may have one or more substituents, but conveniently there are no substituents.

Preferably the cation ii) is derived from an α-amino acid. The basicity may be provided by the extra amino group.

The basic amino group may be alkylated, e.g. with methyl or ethyl groups and thus be present as a secondary or tertiary amino group. The alkylene bridge between the carbon atom to which the carboxylic group and α-amino group is attached and the second amino group preferably contains 3 to 4 carbon atoms, e.g. is lysine.

The invention especially relates to acid addition salts of an amide of taurine or glycine, with a carboxylic acid residue which contains the structure of a 3α, 7α, 12α-trihydroxysteroid, and a basic amino acid.

Amides of taurine or glycine with a carboxylic acid residue which contains the basic structure of a 3α, 7α, 12α-trihydrosteroid are generally known, e.g. from Kirk-Othmers Encyclopedia of Chemical Technology, second Edition Vol. 3, pages 480–488, especially page 481 or from European patent application no. 128,831. They possess in their molecule the basic structure of formula I

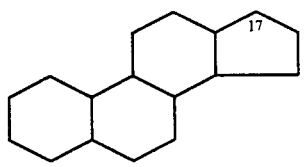

of a steroid with e.g. a saturated, branched $C_4$ alkyl moiety or a branched $C_7$ alkyl moiety having one or two unsaturated bonds, in position 17, which have a carbonyl function $-C(=O)-$ as a substituent, which is linked as an amide with taurine ($-NH-CH_2-CH_2-SO_3H$) or with glycine ($-NH-CH_2-COOH$). The basic structure has other substituents in other positions, especially hydroxyl and methyl groups.

Preferably the taurine or glycine amide is taurocholic or glycocholic acid.

The process of the invention may be effected in conventional manner, e.g. for salt formation.

If desired reactive derivatives of the taurine or glycine and/or amine may be used.

The reaction may be viewed as a neutralization. The acid addition salts of the invention are preferably slightly basic.

The acid addition salts are preferably prepared by combining taurine or glycine, their amino group being amidated with the carboxylic acid residue, in a solvent, preferably a polar solvent, e.g. water, with an aliphatic amine or with a basic amino acid which contains a basic amino group which is connected with the α-amino carboxylic acid group over an alkylene bridge, after which the formed salt is recovered.

Recovering is preferably carried out by freeze drying.

One acid addition salt of a basic amino acid with taurine which is conjugated with a carboxylic acid is known. It is the salt of mono[2-[[(3-alpha, 5-beta, 7-alpha, 12-alpha)-3,7,12-trihydroxy-24-oxochlan-24-yl]amino]-ethanesulfonate, known as taurocholic acid, with 2-arginine and it is described in the Japanese patent application no. 84141510 as a component of a mixture that is used for cosmetic preparations or in food compositions. There is no hint of its use for medicines.

The invention especially provides acid addition salts of an amide of taurine or glycine, with a carboxylic acid as described before, and the basic amino acid lysine $H_2N-(CH_2)_4-CH(NH_2)-COOH$. Lysine may be present as the D- or as the L-form or as a mixture of both forms, e.g. as a racemate.

Preferred acid addition salts with lysine are those with taurine or glycine conjugated carboxylic acids, the anions having the formula II

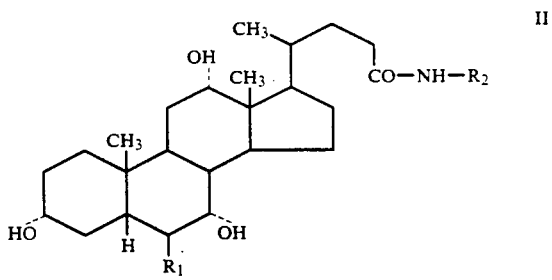

in which
  $R_1$ is H or OH and
  $R_2$ is $-CH_2-COO^-$ or $-CH_2-CH_2-SO_3^-$
and the cation having the formula

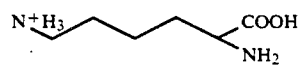

In the cationic salt part the COOH and the $NH_2-$ group behave as usual in amino acids: they may be subjected to Zwitterion formation.

Preferably $R_1 = H$, and $R_2 = -CH_2-CH_2-SO_3^-$.

In the acid addition salts lysine can be present in D- or L-form or as a mixture of both, e.g. as a racemate.

The acids, which are part of the acid addition salts, are also called as taurocholic acids or glycocholic acids and are e.g. obtained from natural human or animal sources or be synthetically produced.

An example of a compound of the invention is the acid addition salt of taurocholic acid with lysine also known as taurocholic acid-lysinate.

In the German Patent Application DE 3623 747 A1 are $3\alpha$, $12\alpha$-dihydroxy tauro or glyco cholanic acids and their alkali salts described, which in position 7 have a $\beta$-hydroxy or particularly the $7\beta$-4'aminobenzamido group, which compounds are, due to their special structure, used for the selective isolation and characterization of proteins from biological membranes.

In another aspect the present invention provides a pharmaceutical composition containing at least one pharmacologically active agent and acid addition salt of an aliphatic amine or a basic alpha amino acid. These are hereinafter referred to as pharmaceutical compositions of the invention.

We have now discovered that such acid addition salts surprisingly are particularly useful as an excipient in pharmaceutical compositions, which contain active agents, e.g. peptide or proteinic drug compounds, and have a resorption promoting influence on such active agents.

In another aspect the invention provides such an acid addition salt, e.g. an acid addition salt of the invention, as an excipient in pharmaceutical compositions contain at least one active agent.

In a further aspect the invention provides a process for the production of a pharmaceutical composition which comprises working up an acid addition salt or an anion of taurine or glycine wherein the amino group thereof is substituted by an acyl group of a $3\alpha$, $7\alpha$, $12\alpha$-trihydroxy steroid carboxylic acid and a cation of either (a) an aliphatic amine, any substituents of which are other than a carboxyl group or (b) a basic alpha amino acid.

The pharmaceutical compositions may be produced in conventional manner, using as desired appropriate excipients, for the route of administration contemplated, e.g. oral, rectal or nasal.

Such compositions conveniently may be prepared by conventional techniques to be in conventional forms, for example, capsules, tablets, suppositories, dispersible powders, syrups, elixirs, suspensions or solutions, for e.g. enteral administration. Suitable pharmaceutical diluents or carriers are described in the examples hereinafter. They may be, for example, water, or hardened oils and waxes, lactose as well as suitable preserving agents, suspending agents, wetting agents, granulating and disintegrating agents, binding agents, lubricating agents in order to provide an elegant and palatable pharmaceutical preparation.

Compositions for inhalation therapy may be prepared in conventional manner, e.g. in the form of nebulizers, vaporizers and aerosols. Unit doses may be provided by a metered valve system. The pharmaceutical compositions of the invention are conveniently prepared for nasal administration. Sodium chloride has been found to be an especially interesting excipient for aqueous nasal compositions, e.g. present in amounts of from 1 to 15 mg/ml.

Conveniently the compositions are in unit dosage form or may be divided into unit dosages each containing, e.g. from about 0.1 to about 100 mg of acid addition salt, the exact amount depending on e.g. the active agent, and the mode of administration. Conveniently the weight ratio of acid addition salt of the invention to the active agent is e.g. from about 1:1 to about 1: 5000.

The invention also provides acid addition salts, the anionic salt part having the formula II, the cationic salt part being that of another basic amino acid, as excipients in pharmaceutical compositions, which contain peptide or protein drug compounds.

The basic amino acids may be present in D- or L-form or as a mixture of both optically active forms, e.g. as a racemate.

Besides acid addition salts of lysine, such of arginine, ornithine and delta-oxylysine are also usable as excipients. However, preferred are acid addition salts of lysine.

The exact dose of pharmacologically active agent may be ascertained in conventional animal or clinical studies. For example, the dose may be ascertained by comparative bioavailability trials with other formulations with a known therapeutic effect, the dose being chosen to produce in the steady state comparable drug plasma levels to therapeutically effective levels. In general, the dose of active agent is from about one half to about one tenth of the dose of active agent in a comparable formulation for the same mode of administration, but without containing a resorption promotor. Indicated doses of peptides are from about 2 micrograms to about 20 mg.

The acid addition salts of the invention and those used in the pharmaceutical compositions of the invention are not only usable in combination with higher molecular water insoluble peptide drug compounds, e.g. Sandimmun ® (cyclosporin A). They are preferably combined with lower molecular peptide drug compounds, e.g. somatostatins, e.g. SMS or especially with calcitonins, e.g. salmon calcitonin.

They are e.g. usable in a quantity of 0.1 to 10, preferably of 0.7 to 1.5% of weight as excipients in pharmaceutical compositions.

Peptide or protein drug compounds with a molecular weight ranging from 1,000 to 150,000 are preferably used in combination with the acid addition salts of the invention.

Usable physiologically active peptides are for instance, peptide hormones like insulin, angiotensin, vasopressin, desmopressin, felypressin, protirelin, luteinizing hormone releasing hormone, corticotropin, prolactin, somatropin, thyrotropin, luteinizing hormone, cyclosporin A (Sandimmun ®), calcitonin, somatostatin, kallikrein, parathyrin, glucagon, oxytoxin, gastrin, secretin, serum gonadotropin, growth hormone, erythropoietin, angiotensin, urogastrone and renin; usable physiologically active proteins are interferon, interleukin, transferrin, histaglobulin, macrocortine and blood coagulation factor VIII; enzyme proteins like lysozyme and urokinase; vaccines like acellular and cellular pertussis vaccine, diphtheria vaccine, tetanus vaccine, influenza vaccine; and toxoids as diphtheria toxoid, tetanus toxoid and toxoids of lymphocytosis promoting factor. Of the polypeptides mentioned above, peptide hormones, physiologically active proteins and vaccines are preferred and peptide hormones are especially more preferred and among these peptide hormones, calcitonins, somatostatins, insulin, luteinizing hormone releasing hormone, desmopressin, vasopressin and oxytocin are particularly desirable and calcitonins and somatostatins are more particularly preferred.

active peptide which exhibit a qualitatively similar effect to that of the unmodified somatostatin peptide.

Preferred somatostatins are:

a) (D)Phe—Cys—Phe—(D)Trp—Lys—Thr—Cys—Thr—ol
(Generic name Octreotide)

b) (D)Phe—Cys—Tyr—(D)Trp—Lys—Val—Cys—ThrNH₂ c) (D)Phe—Cys—Tyr—(D)Trp—Lys—Val—Cys—TrpNH₂ d) (D)Trp—Cys—Phe—(D)Trp—Lys—Thr—Cys—ThrNH₂ e) (D)Phe—Cys—Phe—(D)Trp—Lys—Thr—Cys—ThrNH₂ f) 3-(2-(Naphthyl)-(D)Ala—Cys—Tyr—(D)Trp—Lys—Val—Cys—ThrNH₂ g) (D)Phe—Cys—Tyr—(D)Trp—Lys—Val—Cys-β-Nal—NH₂ h) 3-(2-naphthyl)-Ala—Cys—Tyr—(D)Trp—Lys—Val—Cys-β-Nal—NH₂ i) (D)Phe—Cys-β-Nal—(D)Trp—Lys—Val—Cys—Thr—NH₂

The term "somatostatins" includes its analogs or derivatives thereof. By derivatives and analogs is understood straight-chain, bridged or cyclic polypeptides wherein one or more amino acid units have been omitted and/or replaced by one or more other amino radical(s) of and/or wherein one or more functional groups have been replaced by one or more other functional groups and/or one or more groups have been replaced by one or several other isosteric groups. In general, the term covers all modified derivatives of a biologically Other preferred somatostins are:

H—Cys—Phe—Phe—(D)Trp—Lys—Thr—Phe—Cys—OH
(See Vale et al., Metabolism. 27, Supp.1, 139 (1978)).

Asn—Phe—Phe—(D)Trp—Lys—Thr—Phe—Gaba (See European Pat. Publication No. 1295 and Appln. No. 78 100 994.9).

MeAla—Tyr—(D)Trp—Lys—Val—Phe (See Verber et al., Life Sciences, 34, 1371-1378 (1984) and European Pat. Appln. No. 82106205.6 (published as No. 70 021)) also known as cyclo (N—Me—Ala—Tyr—D—Trp—Lys—Val—Phe).

NMePhe—His—(D)Trp—Lys—Val—Ala (See R.F. Nutt et al.,. Klin. Wochenschr. (1986) 64 (Suppl. VII)

H—Cys—His—His—Phe—Phe—(D)Trp—Lys—Thr—Phe—Thr—Ser—Cys—OH
(see EP-A-200, 188).

The contents of all the above publications including the specific compounds are specifically incorporated herein by reference.

The term analog includes also the corresponding derivatives bearing a sugar residue.

When somatostatins bear a sugar residue, this is preferably coupled to a N-terminal amino group and/or to at least one amino group present in a peptide side chain, more preferably to a N-terminal amino group. Such compounds and their preparation are disclosed, e.g. in WO 88/02756.

A particularly preferred known compound is $N^\alpha$-[α-glucosyl-(1-4-deoxyfructosyl)]-DPhe-Cys-Phe-DTrp-Lys-Thr-Cys-Thr-ol.

The somatostatins are indicated for use in the treatment of disorders with an aetiology comprising or associated with excess GH-secretion, e.g. in the treatment of acromegaly as well as in the treatment of diabetes mellitus. and for use in the treatment of gastro-intestinal disorders, for example, in the treatment of peptic ulcers, enterocutaneous and pancreaticocutaneous fistula, irritable bowel syndrome, dumping syndrome, watery diarrhea syndrome, acute pancreatitis and gastrointestinal hormone secreting tumors (e.g. vipomas, glucagonomas, insulinomas, carcinoids and the like) as well as gastro-intestinal bleeding.

Another preferred class of active agents are calcitonins.

The calcitonins are a known class of pharmacologically active, long chain polypeptides and have different, well documented pharmacological effects. The class does not only contain the natural existing, by extraction obtainable calcitonins, like human, salmon, swine, chicken and cow calcitonin, but also several synthetically prepared derivatives and analog, e.g. such, in which one or more amino acid residues or one or more amino acid sequences which occur in natural products, are omitted, replaced, reversed or in another manner derived or in which the N- or C-terminal residue is modifed. Several calcitonins, e.g. human and salmon calcitonin and the eel calcitonin like Elcatonin are commercially available and are generally used, e.g. for the treatment of the Paget-illness, of hypercalcemia and of osteoporosis.

As generally known for peptides, also the development of appropriate and effective calcitonin adminstration forms has caused many problems. Being peptides, the calcitonins are easily decomposed by the indigestion juices after oral administration. Moreover, they pass the mucuous membranes in the body, whether in the stomach or intestines or in the mouth, the nose or the rectum, difficultly.

A nasal adminstration of fish calcitonin, e.g. salmon calcitonin and an oral inhalation composition have been proposed in the UK Patent 1,354,525, p.3, 1.9-12, but no exact details of a possible composition for nasal use has been described. No details were given whether a resorption promotor was used.

We have now discovered that when pharmaceutical compositions of the invention are used, the passage of the active agents, e.g. peptides, through the mucous membrane and thus the bioavailability may be comparable with that when other resorption promoters are used e.g. sodium taurocholate and when sodium chloride is present it may be improved. Additionally, the novel resorption promoters of the invention have the advantage of an improved local tolerability, when the pharmaceutical compositions containing them are administered onto the nasal mucous membrane. They may not cause mucuous membrane irritations and no significant decrease of the ciliar beat frequency can be established.

The invention thus also provides such acid addition salts in a pharmaceutical composition, which is adapted for the transmucuous transport of peptide drug compounds, preferably for nasal administration. The invention also provides the pharmaceutical compositions containing them.

The pharmaceutical compositions are, if a nasal application is desired, preferably in a powdery or in a liquid condition and are then especially applicable from an atomizer. Representative atomizers are known per se.

The dose of active agent, e.g. peptide drug to be administered by the composition invention is of course dependent on the nature of the active agent, on the type of illness to be treated, of the desirable dose frequency and the desired effect type.

As mentioned in the following Example 4, the bioavailability of the calcitonins, especially of salmon calcitonin (determined by measuring the plasma concentration) after nasal application according to the instructions of the instant invention is high and generally beyond 400% of the values, found after application without resorption promoter or 67% of the value measured with the best known however hardly tolerable resorption promoter, which has a bioavailability of 600%. Consequently the dose to be applied according to the invention is about up to 4 times less than the dose which is necessary for the treatment without resorption promoter.

Up to now doses of about 10 to 400 I.U. were administered once-a-day to 3 times a week of calcitonins, when applied nasally with a known resorption promotor.

For the nasal application according to the invention doses of about 10 to about 400 I.U., preferably of about 50 to about 200 I.U. are necessary, if administered about once-a-day to about three times a week. Suitably, the doses are administered at once. Alternatively, the indicated doses can be divided over 2 to 4 applications per day, which means that for every administration doses of about 2.5 to about 200, preferably about 12.5 to about 100 I.U. are necessary.

The total volume of the composition for a nasal administration is, when in liquid form, preferably about 0.01 to 0.15 ml, especially about 0.1 ml, e.g. 0.09 ml. The compositions of the invention then, at dose volumes of 0.1 ml, preferably contain 10 to about 400, more preferably, about 50 to about 400 I.U. of calcitonin e.g. of salmon calcitonin per 0.1 ml.

If applied 2 to 4 times a day, the compositions of the invention preferably should contain about 2.5 to about 200, more preferably about 2.5 to about 200 I.U. per 0.1 ml.

The invention especially provides a pharmaceutical composition according to the invention, for use in the treatment of the Paget-illness, of hypercalcemia or of osteoporosis containing salmon calcitonin.

The invention also provides a method of administering an active agent to a subject, which method comprises administering to said subject an effective amount of a pharmaceutical composition according to the invention.

The invention provides furthermore the use of an acid addition salt of the invention in the manufacture of a pharmaceutical composition.

EXAMPLE 1

Preparation of the taurocholic acid-lysinate salt

Structural formula of the salt

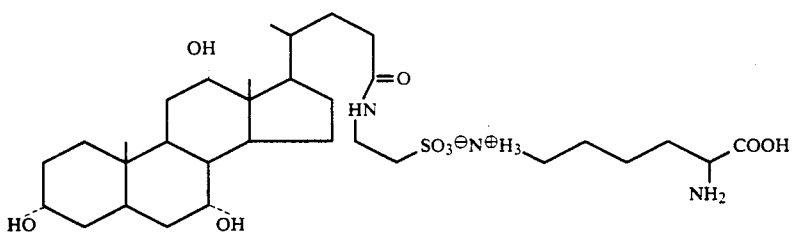

III

1. Preparation of taurocholic acid 10 g of a strongly acid cation exchanger resin was suspended in 50 ml of demineralized water in a chromatography column (length: 30 cm, diameter 1 cm). The resin was rinsed with water until the pH was raised from 1.0 to 6.0.

3 g (0.0056 Mol) of taurocholic acid sodium salt was dissolved in 50 ml of demineralized water and the mixture was applied on the chromatography column. Then the column was washed with 50 ml of demineralized water until pH 6 (neutral) and a clear colorless solution of taurocholic acid was obtained in 100 ml of water of pH 1.0.

2. Preparation of the taurocholic acid—lysinate salt 0.85 g (0.0058 Mol) of L (−)-lysine were dissolved in 100 ml of demineralized water.

The pH of the solution was 13-14. While stirring, the L(−)-lysine solution was added to the taurocholic acid solution. The formation of the salt was followed by titration. The salt solution was lyophilized overnight to obtain a white powder. Melting point 80° C. (sintering). At a temperature of 117° C. the product decomposed.

The pH value of a 0.1N aqueous solution was 8.4. Lysine neutralizes the taurocholic acid considerably stronger as NaOH. (The pH of a 0.1N aqueous sodium taurocholate solution is 6.1).

$^1$H-NMR (D$_2$O) delta (ppm): 4,04 (m,1H,CH—OH); 3,88 (m,1H,CH—OH); 3,69 (A,J=7 Hz, 1H,CH-alpha of lysine); 3,57 (A,J=7 Hz, 2H, CH$_2$—NHCO); 3,49 (m, 1H, CH—OH); 3,07 (t,J=7 Hz, 2H, CH$_2$—SO$_3$−); 3,01 (t,J=7 Hz, 2H, CH$_2$-epsilon of lysine); 2,4-1,05 (m,28H, CH$_2$ and CH of β, gamma, d-lysine and cholic acid residue); 0,98 (d,J=7 Hz, 3H, CH$_3$—CH of the cholic acid residue); 0,91 (s, 3H, C—CH$_3$ of the cholic acid residue); 0,7 (s,3H, C—CH$_3$ of the cholic acid residue).

IR (KBr) cm$^1$; 3400 (S,H$_2$O); 3100-2800 (S,nu (—NH$_3$+); 2070 (W,delta $_{as}$+delta$_{torsion}$ (—NH$_3$+); 1650 (s,delta$_{as}$ (NH$_3$+); 1500 (m,nu$_{as}$ (—COO−); 1410 (m,nu$_{sy}$ (—COO−)); 1220-1150 (s,nu$_{as}$ (—SO$_3$−); 1040 (m,nu$_{sy}$ (—SO$_3$−).

nu is the indication of the greek letter ν

EXAMPLE 2

Solutions for nasal application

| | |
|---|---|
| Salmon calcitonin | 110 I.U. to 4400 I.U. |
| Sodium citrate - dihydrate | 10.0 mg |
| Citric acid - monohydrate | 10.0 mg |
| Taurocholic acid - lysinate | 10.0 mg |
| Ethylenediaminetetraacetic acid | 1.0 mg |
| disodium salt | |
| Benzalkonium chloride | 0.2 mg |
| Water up to | 1.0 ml |

This solution was drawn off in an atomizer and sprayed in a quantity of 0.09 ml per nostril. (The dosage quantity per nostril is e.g. about 10 I.U.).

Instead of salmon calcitonin other polypeptides, e.g. other calcitonins can be formulated in quantities of e.g. up to 4400 I.U. per ml. Also a somatostatin can be formulated in this manner.

EXAMPLE 3

Solutions for nasal application:

| | |
|---|---|
| Salmon calcitonin | 110 I.U. to 4400 I.U. |
| Benzalkonium chloride | 0.11 mg |
| Sodium chloride | 8.5 mg |
| Taurocholic acid - lysinate salt | 10.0 mg |
| HCl 0.1N up to pH 3.7 | |
| Water up to | 1.0 ml |
| Nitrogen atmosphere | |

The solution was filled in an ampule and is suitable for application of dosage quantities of 0.09 ml (dosage per nostril e.g. 10 I.U.).

Instead of salmon calcitonin other polypeptides e.g. other calcitonins can be formulated in quantities of up to e.g. 4400 I.U. per ml.

EXAMPLE 4 a) A dose of 100 I.U. of salmon calcitonin per 0.09 ml of an aqueous solution according to Example 2 was applied and compared with.

b) a comparable dose, which contained 1% of weight of sodium taurocholate a very effective known resorption-promotor instead of the taurocholic acid lysinate salt and with c) another comparable dose, which did not contain any resorption promotor.

The results are plotted in FIG. 1 and are expressed as milli-international units of salmon calcitonin per ml plasma versus the application term in hours and in which the curves a, b and c correspond to the applied mixtures described above. The drug compound concentration was measured in the plasma by radio-immuno-assay.

The salmon calcitonin determinations were carried out up to 6 hours after application.

The doses were under comparable conditions applied to both the nostrils of three rhesus monkeys, which means that totally 200 I.U. of salmon calcitonin were applied per test animal.

The bioavailability was calculated over the first application term of 1 hour and was related to the reference under c (=100%):

| a | b | c |
|---|---|---|
| 429% | 637% | 100% |

The local tolerances were measured in two experiments 1. and 2. with composition a, and in one experiment with composition b and c measured with microphotooscillography* and were expressed as Hz (Hertz). The results were compared with the frequency of non-treated animals (control experiment).

* after 28 days of nasal application in guinea-pigs

|   | a | b | c | control experiment |
|---|---|---|---|---|
| 1. | 12.59 Hz ± 0.05 | 0 | 10.55 ± 0.91 | 11.95 ± 0.58 |
| 2. | 11.60 Hz ± 1.30 | 0 |   |   |

The experiment is described in detail in the following articles:

Nasal brushing and measurement of ciliary beat frequency. An in vitro method for evaluating pharmacologic effects on human cilia Rutland J., Griffin W., Cole P. in: Chest 80, 6 Dec. 1981, Supplement; Die Wirkung von Bronchospasmolytika auf die Ciliarfrequenz in vitro, Nonietzko N., Kasparek R., Kellner U., Petro J.: Prax. Klin.Pneumol 37, (1983) 904–906.

The oscillation frequency was not influenced with the composition a of the invention and with composition c without resporption promoter. With composition b which contained a known resorption promoter the oscillation was blocked.

CONCLUSION

The bioavailability of salmon calcitonin, when applied in combination with the resorption promoter according to the invention is, with regard to the normal biological variation, as good as when applied in combination with sodium taurocholate. The advantage of the resorption promoter according to the invention over this promoter is its excellent tolerability, which means a considerable progress.

EXAMPLE 5

Capsules for oral application

| Salmon calcitonin | 0.1 to 20 mg* |
|---|---|
| Taurocholic acid lysinate salt | 50 mg |
| Microcrystalline cellulose | 100 mg |
| Lactose | 50 mg |

*1 mg of drug compound corresponds to 4767 I.U.

EXAMPLE 6

Suppositoria for rectal application

| Salmon Calcitonin | 0.0692 mg |
|---|---|
| anhydrous citric acid | 0.78 |
| Trisodium citrate-dihydrate | 0.50 |
| Mannitol | 48.651 |
| Taurocholic acid-lysinate salt | 30.0 |
| Suppositorium base A* | 1420.0 |
| | 1500.0 mg |

*Witepsol ® H.12, a linear (C₁₀-₁₈) fatty acid glyceride. Melting range 32-33.5°, solidification range 29-33° C. Obtainable from Dynamit Nobel, Germany.

We claim:

1. An acid addition salt of an anion (i) of taurine or glycine wherein the amino group thereof is substituted by an acyl group of a 3α,7α,12α-trihydroxy steroid carboxylic acid and a cation (ii) of either (a) an aliphatic amine any substituents of which are other than carboxyl groups or (b) a basic alpha amino acid having an alkylene bridge between the alpha amino acid group and another amino group.

2. A salt of claim 1 wherein the anion is derived from taurocholic or glycocholic acid.

3. A salt of claim 1 wherein the cation is derived from a basic alpha amino acid having an alkylene bridge between the alpha amino acid group and another amino group.

4. A salt of claim 3 wherein the cation is derived from lysine.

5. An acid addition salt of an anion of formula II

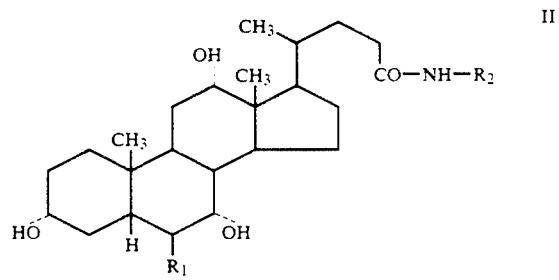

in which
$R_1$ = H or OH and
$R_2$ = —$CH_2$—$COO^-$ or —$CH_2$—$CH_2$—$SO_3^-$
and a cation having the formula

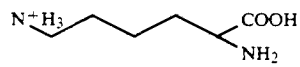

6. A salt of claim 5 wherein $R_1$ is hydrogen.

7. A salt of claim 6 wherein $R_2$ is —$CH_2$—$CH_2$—$SO_3^-$.

8. A pharmaceutical composition comprising at least one pharmacologically active agent and an acid addition salt of claim 1.

9. A composition according to claim 8 wherein the pharmacologically active agent is a calcitonin.

10. A composition according to claim 8 wherein the ratio of acid addition salt to pharmacologically active agent is from 1:1 to 5000:1.

11. A composition according to claim 8 in unit dosage form containing from about 0.1 to 100 mg of the acid addition salt.

12. A composition according to claim 8 in nasal form.

13. A composition according to claim 8 comprising an acid addition salt of an anion of formula II

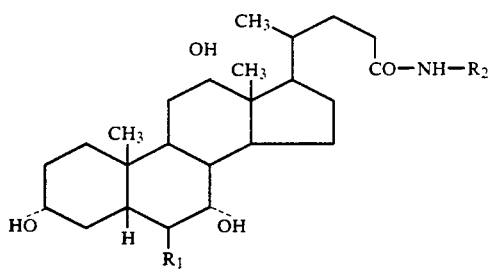
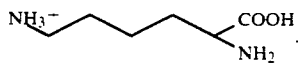
wherein
R₁ is hydrogen or hydroxy, and
R₂ is $-CH_2-COO^-$ or $-CH_2-CH_2-SO_3^-$,
and a cation having the formula
14. A composition according to claim 13 wherein $R_1$ is hydrogen.
15. A composition according to claim 14 wherein $R_2$ is $-CH_2-CH_2-SO_3^-$.